United States Patent [19]

Harvey et al.

[11] Patent Number: 4,546,161

[45] Date of Patent: Oct. 8, 1985

[54] MEDIA FOR AFFINITY CHROMATOGRAPHY

[75] Inventors: Michael J. Harvey, St. Albans; Anthony Atkinson, Salisbury, both of England

[73] Assignee: The Secretary of State for Defence in Her Britannic Majesty's Government of the United Kingdom of Great Britain and Northern Ireland, London, England

[21] Appl. No.: 545,546

[22] Filed: Oct. 26, 1983

Related U.S. Application Data

[63] Continuation-in-part of Ser. No. 165,481, Sep. 19, 1979, abandoned.

[30] Foreign Application Priority Data

Jan. 24, 1978 [GB] United Kingdom ............... 2878/78
Jan. 27, 1978 [GB] United Kingdom ............... 3505/78

[51] Int. Cl.$^4$ .................... C08B 31/00; C08B 37/02
[52] U.S. Cl. .................... 527/312; 527/300; 436/528; 436/529; 436/531; 435/178; 435/180; 260/112 R; 536/45; 536/51
[58] Field of Search ............. 525/54.1, 54.31; 527/300, 312; 436/528, 529, 530, 531; 435/178, 179, 180; 260/112 R; 536/51, 45

[56] References Cited

U.S. PATENT DOCUMENTS

| 3,304,297 | 2/1967 | Wegmann et al. | 536/46 |
| 3,403,146 | 9/1968 | Hunt | 536/46 |
| 3,619,371 | 11/1971 | Crook et al. | 424/85 |
| 4,144,128 | 3/1979 | Hildebrand et al. | 260/121 |
| 4,385,991 | 5/1983 | Rosevear et al. | 210/656 |
| 4,431,546 | 2/1984 | Hughes et al. | 210/656 |

Primary Examiner—John Kight
Assistant Examiner—Nathan M. Nutter
Attorney, Agent, or Firm—Stevens, Davis, Miller & Mosher

[57] ABSTRACT

Affinity chromatography media are prepared by reacting mono or di-chloro triazine dyes with a solid support matrix containing free hydroxy or amino groups in the presence of an alkali metal hydroxide and an alkali metal salt. In the absence of cyanogen bromide activation, the linkage to the support is entirely via the triazine ring giving high and specific protein-binding capacity. Suitable support matrices include polymers and copolymers of agarose, dextrose, dextran and acrylamide with agarose being particularly preferred. Dye binding levels are much higher than those obtained in the presence of carbonates or bicarbonates.

Mono-chlorotriazinyl dyes are bound at a pH which is preferably above 9.5. The reaction time is about 40–60 hours at room temperature, however this may be reduced if the reaction temperature is increased. Dichlorotriazinyl dyes are bound at pH 8 to 12.5 in a few hours at room temperature.

The media may be used for the efficient and often highly specific purification of a wide variety of proteins, including enzymes and blood proteins.

12 Claims, 1 Drawing Figure

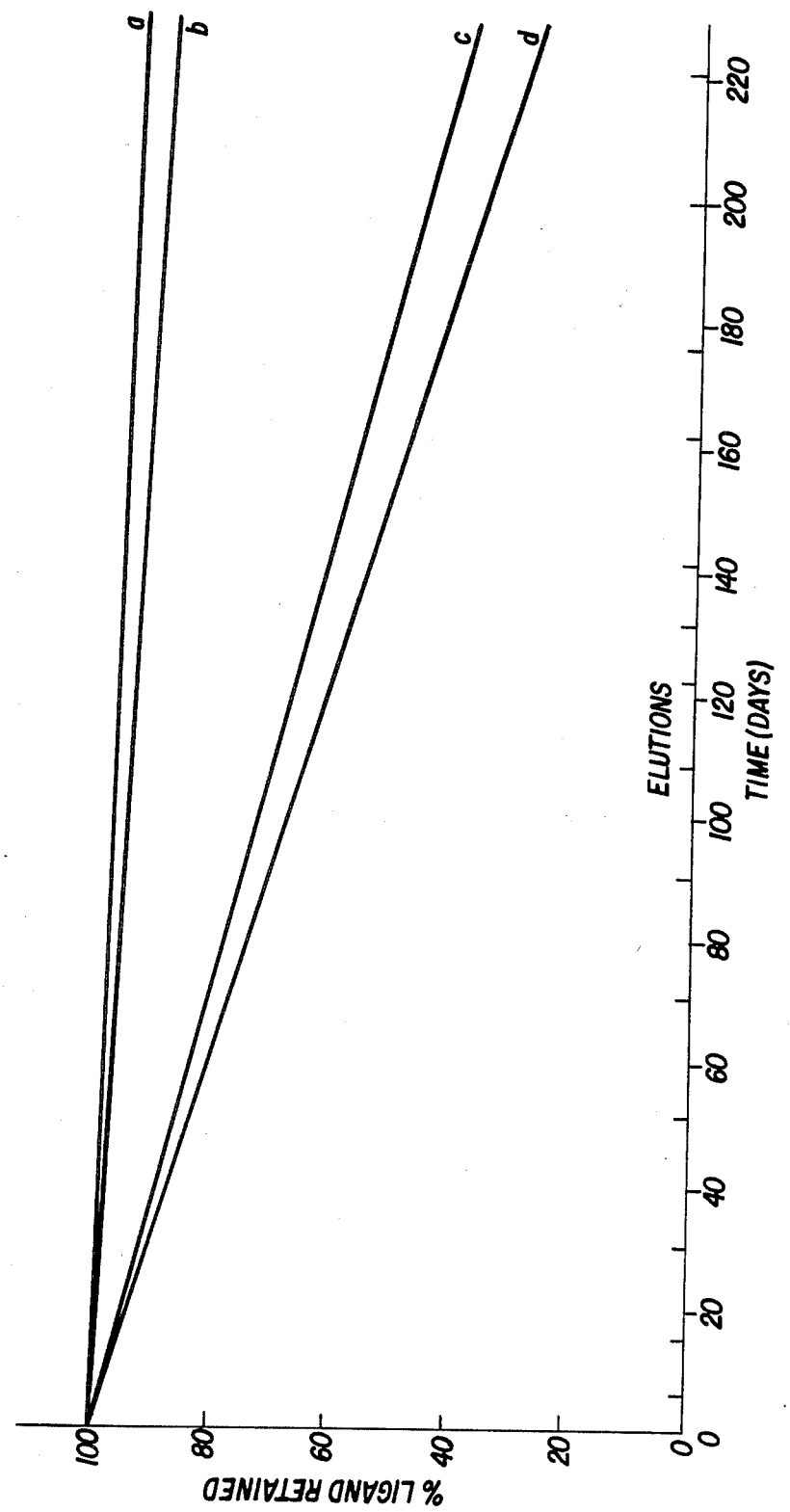

MEDIA FOR AFFINITY CHROMATOGRAPHY

This application is a continuation-in-part of U.S. application Ser. No. 165,481, filed Sept. 19, 1979 and now abandoned, itself based on international application No. PCT/GB 79/00016, filed Jan. 22, 1979.

BACKGROUND OF INVENTION

The invention relates to protein-binding media for affinity chromatography and especially to solid media having high specific protein-binding capacity.

Affinity chromatography involves separation of proteins by selective absorption onto and/or elution from a solid medium, generally in the form of a column. The solid medium is generally an inert carrier matrix to which is attached a ligand having the capacity to bind under certain conditions the required protein or proteins in preference to others present in the same sample, although in some cases the matrix itself may have such selective binding capacity. The ligand may be biologically complementary to the protein to be separated, for example antigen and antibody, or may be any biologically unrelated molecule which by virtue of the nature and steric relationship of its active groups has the power to bind the proteins.

There are described in, for example, U.S. Pat. No. 4,016,149 and by Baird et al, Febs Letters, Vol 70 (1976) page 61, solid media wherein the ligands are monochloro-triazinyl dyes which are bound to dextran or agarose matrices by substitution of the chloride substituent. Such binding is carried out in sodium carbonate or bicarbonate buffered media and since the dyes are designed for dying cellulose, the bound dye concentrations on non-cellulosic matrices are generally very low resulting in low protein binding capacity. It is possible to increase the dye binding by cyanogen bromide activation of the agarose matrix. However cyanogen bromide activation has serious disadvantages, especially for industrial use: the material is highly toxic and hence too dangerous to use on an industrial scale; it produces amido carbonate and carbamate links with the matrix which are unstable and cause gradual loss of column activity in long-term use; and it activates hydroxyl and amine groups on the dye resulting in dye-dye bonding and dye-bonding other than through the triazine group so that only a small proportion of the bound dye molecules are available for protein binding and their protein binding properties may differ. In addition, it is sometimes found that columns with very high bound dye contents bind protein so firmly that elution is not practicable. Moreover cyanogen bromide activation cannot be used for immobilisation of dichloro-triazinyl dyes.

A further class of solid media are prepared by linking monochloro-triazinyl dyes to dextran and then to agarose supports. In this case the chlorine substituent on the triazine ring is replaced by an -O-dextran linkage and linkage to the support is entirely via other reactive, especially amine, groups on the dye following cyanogen bromide activation. Hence the binding specificity again differs from media wherein the binding is via the triazine ring, and the media suffer all the disadvantages discussed above in respect of cyanogen bromide activation.

There is thus a need for a method of achieving useful controlled levels of dye binding without the use of cyanogen bromide.

The present invention provides a process for producing a protein binding solid medium, said process comprising reacting a protein binding ligand material of structure

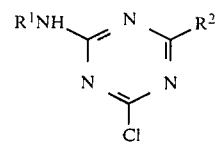

wherein $R^1$ is a sulphonated derivative of anthraquinone, a substituted anthraquinone, an aromatic azo group or a phthalocyanine group, and $R^2$ is either an organic group or a chloro substituent, with an affinity chromatographic matrix containing hydroxy or amino groups which is a polymer or copolymer of agarose, dextrose, dextran or acrylamide, at a pH of at least 8, in an aqueous solution of an alkali metal hydroxide and an alkali metal salt wherein the salt enhances the binding of the ligand material to the matrix by a common ion effect.

In the case of monochlorotriazinyl ligands ($R^2$ is an organic group) useful levels of dye binding may also be achieved in the absence of the alkali metal salt.

It has surprisingly been found that the use of an alkali metal hydroxide in this reaction, particularly if the use is in conjunction with a suitable alkali metal salt, results in a much higher level of binding of the ligand to the matrix than occurs if the reaction is conducted under similar conditions of temperature, time and base concentration but in the presence of an alkali metal carbonate or bicarbonate. Furthermore, the media produced by the present process show tighter elution profiles than their carbonate/bicarbonate produced counterparts.

The alkali metal hydroxide may be any Group I metal hydroxide. Generally however the more readily available hydroxide bases such as potassium and, which is particularly preferred, sodium hydroxide will be employed.

The alkali metal salt may be any Group I metal salt which, in conjunction with the chosen alkali metal hydroxide, enhances the binding of the ligand material to the matrix by a common ion effect. Examples include potassium chloride, sodium sulphate, di-sodium hydrogen phosphate, sodium nitrate and, which is particularly preferred, sodium chloride.

In a preferred embodiment of the present process the ligand material and the matrix are first mixed in a suitable solvent in the presence of the alkali metal salt. The alkali metal hydroxide is then added and the binding reaction allowed to proceed.

The ligand material is a triazinyl dye, especially those sold under the Trade Marks "Cibacron" and "Procion". In one preferred embodiment of the present invention $R^1$ is a sulphonated derivative of anthraquinone or a substituted anthraquinone. In this case $R^1$ may be a derivative of structure

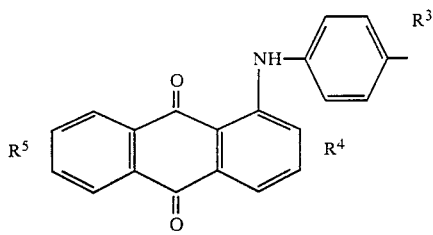

wherein $R^3$, $R^4$ and $R^5$ each represent a sulphonyl group or a hydrogen atom. Optionally such a derivative may be further substituted by alkyl or amino groups.

In an alternative preferred embodiment $R^1$ is a sulphonated derivative of an aromatic azo group. In this case $R^1$ may be a derivative of structure

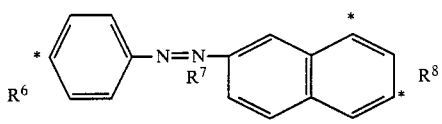

wherein $R^6$, $R^7$ and $R^8$ each represent a sulphonyl group or a hydrogen atom and the point of attachment to the triazinyl ring may be any of the points marked "*", Optionally such a derivative may be further substituted by other suitable substituent groups.

$R^2$ may be either an organic group or a chloro substituent. In the former case $R^2$ is preferably a sulphonated aromatic, particularly a sulphonated phenyl, group.

Examples of triazinyl dyes that may advantageously be employed in the process of the present invention are the Cibacron dyes manufactured by Ciba Ltd and the Procion dyes manufactured by ICI. Illustrative of these dyes are Cibacron Orange G-E, Cibacron Brillant Blue FBR-P,
Cibacron Blue F3G-A, Cibacron Brillant Red 3B-A,
Cibacron Brown 3 GR-A, Cibacron Scarlet 2G, Cibacron Scarlet 4G-P,
Cibacron Brillant Red B-A, Procion Brillant Orange HGRS,
Procion Blue HBS, Procion Brillant Red H7BS, Procion Orange
Brown HGS, Procion Scarlet H3GS, Procion Red H3B, Procion Red HE3B,
Procion Red P3BN, Procion Red MX2B, Procion Blue MX3G,
Procion Yellow MXR, Procion Yellow H5G, Procion Red H8BN,
Procion Green H-4G, Procion Brown MX5BR, Procion Blue MX-G,
Procion Blue HE-RD, Procion Blue H-B, Procion Blue MXR,
Procion Yellow HA and Procion Green HE-4BD.

When commercial dyes are used it may be necessary to remove wetting agents by, for example, washing with ether or acetone.

The matrix is a polymer or copolymer of agarose, dextrose, dextran or acrylamide, with an agarose homopolymer being particularly preferred. (NB. Cellulose and substituted celluloses are unsuitable as matrices since although they bind large quantities of dye, this is poorly accessible to protein during chromatography resulting in poor protein binding.)

The optimum concentration of alkali metal hydroxide depends on the structure of the ligand. For mono-chloro-triazinyl derivatives ($R^2$=an organic group) the pH should be at least 9.5 to achieve an optimum coupling. Normally the alkali concentration should be 0.02 to 0.4, preferably 0.05 to 0.2N, although the upper limit is not particularly critical.

With dichloro-triazinyl derivatives ($R^2$=chlorine) the alkali concentration should be about 0.002 to 0.1, preferably 0.005 to 0.01N (pH about 8 to 12.5) and the ligand binding is found to fall off quite rapidly once an optimum alkali concentration is exceeded.

The ligand-matrix coupling reaction may be conducted over a wide range of temperature, within the stability ranges of both reagents, without serious effect on the amount of ligand bound. However the monochloro triazinyl ligands bind only slowly so that at ambient temperatures (15°–25° C.) as long as 40 to 60 hours may be required for optimum reaction, and elevated temperatures of 40° to 60° C. are preferred since they both speed the reaction and yield a media showing a tighter elution profiles. Dichloro-triazinyl-ligands normally react in 1 to 4 hours of ambient temperatures and there appears no significant advantage in using higher temperatures.

The concentration of the alkali metal salt should be high enough to produce an enhancement but not so high as to reverse the effect. Typically the alkali metal salt concentration will be between 0.25 and 0.5 Molar. Such a concentration of sodium chloride at least doubles the amount of dye bound to the matrix (in comparison with the amount of dye bound in the absence as NaCl).

The presence of chloride substituents in the solid medium may have an adverse effect on protein-binding and hence when dichloro-ligands are used in the above process, the process should preferably be followed by a further step to convert any free chloride substituent in the solid medium to a less displaceable group such as amino, hydroxyl or thiol.

The process of the present invention permits much higher concentrations of dye to be bound to the matrix than was possible with previously known non cyanogen bromide based methods. Thus according to a further aspect of the invention there are provided protein-binding solid media comprising a protein-binding ligand containing triazinyl groups bound directly to a matrix and having substantially the structure.

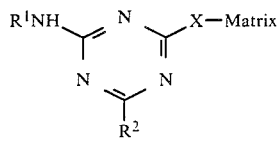

wherein X represents —O— or —NH— and $R^1$ and $R^2$ are as defined above, said ligand being present in a proportion of more than 15 mg preferably at least 30 mg especially at least 45 mg per gm of dry matrix. These figures are for the ligand actually bound as determined by digestion in 50% (v/v) acetic acid followed by spectrophotometry. It should be noted that although these amounts are less than those sometimes quoted in the prior art, the prior art figures refer to the amount of dye added to the reaction mixture not to the amount of dye actually bound to the matrix.

Preferably the matrix is an agarose homopolymer.

In accordance with yet another aspect of the invention, the protein-binding solid media may be used in the conventional manner for the separation and purification of proteins by affinity chromatography. Thus a crude or semi-purified biological material normally in a buffered solution at a concentration of 1 to 20, but exceptionally up to 100, mg protein per ml, is contacted, normally in a column, with the solid medium. After washing the medium the retained protein may be eluted by standard techniques such as by using a solution of different pH, buffer composition or ionic strength, or containing a co-substrate, co-factor, inhibitor, allosteric effector, unbound ligand or chaotrophic reagent or by electrophoresis.

The media of the present invention are capable of performing simple and highly specific purifications of a wide range of proteins, especially blood proteins and enzymes, both animal and bacterial. For example, selected media may be used to purify albumin, kinases such as glycerokinase and especially urokinase, nucleases including restriction endonucleases, dehydrogenases such as glyceraldehyde-3-phosphate dehydrogenase or β-hydroxy-butyrate dehydrogenase, esterases such as cholinesterase, or DNA or RNA binding proteins such as DNA lygase. Because of the high bound-ligand content of the media, the amount of protein which may be separated per gram of medium is very much higher contents may result in excessive binding of the protein and consequent elution difficulties, an effect not encountered at ligand concentrations achieved by the prior art. Thus in these cases optimisation of the ligand content is necessary.

The various aspects of the invention will now be illustrated by reference to specific examples of the preparation and use of protein-binding solid media, wherein all bound-ligand figures are quoted on the basis of weight of media sucked dry on a filter funnel. Thus 15 grm sucked dry medium equals about 25 ml settled volume and 1 grm of fully dried material. It should be noted that the degree of ligand binding varies between dye batches and with the age of the dye so that results of experiments run at different times are not always strictly comparable.

The ligands used in these examples were commercial dyes having the following typical structures and Colour Index Constitution Numbers (CICN). In all cases M may represent a hydrogen atom, but normally represents an alkali metal, usually sodium, ion. All dyes were ether washed before use.

TABLE 1

| LIGAND | CICN No | TRADE NAME | STRUCTURAL FORMULA |
|---|---|---|---|
| A (n = 1) | 18159 | Procion Red H3B | |
| B | — | Procion Red HE3B | As Ligand A, but n = 2 (p-isomer) |
| C | — | Procion Red P3BN | Similar to Ligand A |
| D | 18158 | Procion Red MX2B | |
| E | — | Procion Blue MX3G | |
| F | 13190 | Procion Yellow MXR | |

TABLE 1-continued

| LIGAND | CICN No | TRADE NAME | STRUCTURAL FORMULA |
|---|---|---|---|
| G | 18972 | Procion Yellow H5G | |
| H | 61211 | Cibacron Blue F3GA | |
| I | — | Procion Red H8BN | |

Procion and Cibacron are Trade Marks

PRODUCTION OF SOLID MEDIA

EXAMPLES 1 TO 8

One gm samples of an uncross-linked agarose gel (supplied by Pharmacia Ltd under the trade mark "Sepharose 4B") were slurried in 3.5 ml of water and 1 ml of a 10 mg/ml aqueous solution of ligand A was added to each. The suspensions were mixed for 5 minutes and then 0.5 ml of a 200 g/l aqueous solution of sodium chloride was added, After a further 30 minutes of mixing, 5N sodium hydroxide was added to give final alkali concentrations of 0.4, 0.1, 0.05, 0.02, 0.01, 0.005, 0.002 and 0.001N. The suspensions were mixed for a further 19 hours at room temperature after which they were filtered. The solids were washed copiously with water and a 1 g sample (moist weight as filtered) was digested at 80°–90° C. in 2 ml of 50% (v/v) acetic acid. The ligand content was estimated from the optical density at 520 nm. The results are shown in Table 2.

EXAMPLE 9

The procedure of Examples 1 to 8 was repeated using ligand B and a final NaOH concentration of 0.025N. The result is shown in Table 2.

EXAMPLES 10 TO 14

(Comparative)

Ligand B bound to the matrix of Example 9 using the process described by Baird et al, Febs Letters November 1976 pages 61–66 using sodium carbonate as alkali at final concentrations of 0.002 to 0.2N. The standing times and analysis procedure were as in Example 9. Results are shown in Table 2.

TABLE 2

| EXAMPLE | LIGAND | ALKALI | ALKALI CONC (N) | mg LIGAND/ g MATRIX |
|---|---|---|---|---|
| 1 | A | NaOH | 0.4 | 0.27 |
| 2 | A | " | 0.1 | 0.39 |
| 3 | A | " | 0.05 | 0.39 |
| 4 | A | " | 0.02 | 0.32 |
| 5 | A | " | 0.01 | 0.24 |
| 6 | A | " | 0.005 | 0.135 |
| 7 | A | " | 0.002 | 0.05 |
| 8 | A | " | 0.001 | 0.02 |
| 9 | B | " | 0.025 | 0.196 |
| 10 | B | $Na_2CO_3$ | 0.002 | 0.004 |
| 11 | B | " | 0.006 | 0.015 |
| 12 | B | " | 0.02 | 0.023 |
| 13 | B | " | 0.06 | 0.05 |
| 14 | B | " | 0.2 | 0.067 |

EXAMPLES 15–22

Ligands E and H were attached to either Sepharose 4B or Cellulose by the methods of the present invention or Baird et al (supra) at the optimum final alkali concentration for each system. The results are shown in Table 3.

TABLE 3

| EXAMPLE | LIGAND | MATRIX | ALKALI | FINAL CONC | mg LIGAND/gm MATRIX |
|---|---|---|---|---|---|
| 15 | E | Sepharose 4B | NaOH | 0.025 N | 4.3 |
| 16 | E | " | $Na_2CO_3$ | 0.1 N | 0.4 |
| 17 | E | Cellulose | NaOH | 0.025 N | 9.2 |
| 18 | E | " | $Na_2CO_3$ | 0.1 N | 6.4 |
| 19 | H | Sepharose 4B | NaOH | 0.1 N | 3.0 |
| 20 | H | " | $Na_2CO_3$ | 0.1 N | 0.2 |
| 21 | H | Cellulose | NaOH | 0.1 N | 6.8 |
| 22 | H | " | $Na_2CO_3$ | 0.1 N | 3.9 |

EXAMPLES 23–30

Example 1 was repeated using varying amounts of water and 10 mg/ml ligand solution in order to vary the ligand concentration. The final alkali concentration was 0.025N and the incubation period was reduced from 19 to 17 hours. The results are shown in Table 4.

TABLE 4

| EXAMPLE | WATER (ml) | 10 mg/ml LIGAND soltn (ml) | TOTAL VOLUME[1] (ml) | LIGAND conc (mg/ml) | mg LIGAND/ gm MATRIX |
|---|---|---|---|---|---|
| 23 | 0.5 | 4 | 5.025 | 8 | 0.56 |
| 24 | 1.5 | 3 | 5.025 | 6 | 0.515 |
| 25 | 2.5 | 2 | 5.025 | 4 | 0.44 |
| 26 | 3.5 | 1 | 5.025 | 2 | 0.28 |
| 27 | 4.0 | 0.5 | 5.025 | 1 | 0.15 |
| 28 | 4.3 | 0.2 | 5.025 | 0.4 | 0.06 |
| 29 | 4.9 | 0.1 | 5.525 | 0.18 | 0.02 |
| 30 | 4.95 | 0.05 | 5.525 | 0.09 | 0.01 |

Note 1:
Total Volume includes 0.5 ml 200 g/l NaCl - 0.025 ml 5N NaOH

EXAMPLES 31 AND 32

Example 1 was repeated using a monochloro-triazine ligand, ligand A, and a dichloro-triazine ligand, ligand D, at a final alkali concentration of 0.025N. Samples were withdrawn at various intervals after alkali addition and analysed for ligand content. Results are shown in Table 5.

TABLE 5

| | mg LIGAND/gm MATRIX | |
|---|---|---|
| TIME | EXAMPLE 31 (ligand A) | EXAMPLE 32 (ligand D) |
| 5 mins | 0.006 | 0.59 |
| 10 mins | 0.008 | 0.77 |
| 20 mins | 0.011 | 0.81 |
| 40 mins | 0.022 | 0.81 |
| 80 mins | 0.041 | 0.83 |
| 2 hours | 0.051 | 0.84 |
| 4 hours | 0.095 | 0.85 |
| 20 hours | 0.325 | 0.89 |
| 47 hours | 0.52 | — |
| 69 hours | 0.58 | — |

EXAMPLES 33–38

The procedure of Example 1 was used to bind Ligand E to 1 gm samples of nylon sheet (porosity 30 microns) in the presence of various final concentrations of either sodium hydroxide or sodium carbonate. The amounts of ligand bound were estimated from the residual content of the reaction liquid since the acetic acid digestion procedure cannot be applied to nylon. Results are shown in Table 6.

TABLE 6

| EXAMPLE | ALKALI | FINAL CONC | mg LIGAND/gm MATRIX |
|---|---|---|---|
| 33 | NaOH | 0.025 N | 0.5 |
| 34 | NaOH | 0.1 N | 0.8 |
| 35 | NaOH | 0.5 N | 0.4 |
| 36 | $Na_2CO_3$ | 0.05 N | 0.1 |
| 37 | $Na_2CO_3$ | 0.2 N | 0.1 |
| 38 | $Na_2CO_3$ | 1.0 N | 0.2 |

EXAMPLES 39 TO 42

The process of Example 1 was repeated using ligand B and various matrices at a final sodium hydroxide concentration of 0.025N and mixing for 74 hours. The weights of ligand bound are shown in Table 7.

TABLE 7

| EXAMPLE | MATRIX | mg LIGAND/ gm MATRIX |
|---|---|---|
| 39 | Agarose gel (Sepharose* 4B) | 0.65 |
| 40 | Cross-linked dextran (Sephadex* G100) | 0.63 |
| 41 | Dextran/acrylamide copolymer (AcA 44 Ultragel*) | 0.29 |
| 42 | Cross-linked agarose (Sepharose* 4BCL) | 0.32 |

*Sepharose, Sephadex and Ultragel are Trade Marks

COMPARATIVE TESTS

For purposes of comparison, ligands E, H & I were bound to Sepharose 4B by the methods of the present invention (final alkali conc 0.025N for ligand E and 0.1N for ligands H & I) and of U.S. Pat. No. 4,016,149 and German Application (DOS) P No. 2722970.5 both with and without cyanogen bromide activation. Results are shown in Table 8.

TABLE 8

| Ligand | Cyanogen Bromide activation | mg LIGAND/gm MATRIX | | |
|---|---|---|---|---|
| | | U.S. Pat. No. 4,016,149 | DOS P 27 22 970.5 | Present invention |
| E | NO | 1.0 | 0.4 | 4.3 |
| H | " | 0.5 | 0.4 | 2.9 |
| I* | " | 0.4 | 0.2 | 2.8 |
| E | YES | 5.0 | 5.2 | 5.3 |
| H | " | 5.0 | 5.1 | 5.1 |
| I* | " | 4.9 | 4.9 | 4.8 |

*Related to Brilliant Red 3-BA used in USP 4,016,149

Thus the method of the present invention gives higher bound ligand concentrations than either of the prior art techniques without cyanogen bromide activation and gives ligand binding comparable to that obtainable with cyanogen bromide activation.

The stabilities of the columns of ligands E and I bound to the matrix by different methods were compared by preparing 2 ml columns in 10 mM potassium phosphate (pH 7.5) and storing these at ambient temperature (18°–22° C.). The columns were periodically washed with 20–35 ml of the same buffer and the ligand content of the washings estimated by spectrophotometry. The percentage of ligand remaining on the column was estimated.

The results are shown in the accompanying drawing in which:
  lines a and b show the leaching pattern for columns of ligands E and I respectively bound by the method of the present invention.
  lines c and d shows the equivalent patterns for columns of ligands E and I bound by the method of U.S. Pat. No. 4,016,149 using cyanogen bromide activation.

EXAMPLE 43

An uncrosslinked agarose gel (1 g, supplied by Pharmacia Limited under the trade mark "Sepharose 4B") was slurried in 4 ml of water and 1 ml of a 10 mg/ml aqueous solution of Procion Blue MXR was added. The suspension was stirred for 35 mins and then 5M sodium hydroxide was added to give a final alkali concentration of 0.01M. The suspension was mixed for a further 19 hours at room temperature after which it was filtered. The solid medium was washed with water (5×10 ml) and then a 1 g sample (moist weight as filtered) was digested for 30 mins at 90° C. in 2 ml of 50% (v/v) acetic acid. The ligand content of the solid medium was estimated from the optical density (at 520 nm) of the acetic acid digest.

EXAMPLE 44

An uncrosslinked agarose gel (1 g supplied by Pharmacia Limited under the trade mark "Sepharose 4B") was slurried in 3.5 ml of water and 1 ml of a 10 mg/ml aqueous solution of Procion Blue MXR was added. The suspension was mixed for 5 mins and then 0.5 ml of a 5M aqueous solution of sodium chloride was added to give a final NaCl concentration of 0.5M. After mixing the suspension for a further 30 mins, 5M sodium hydroxide was added to give a final alkali concentration of 0.01M. The suspension was mixed for a further 19 hours at room temperature and then filtered. The solid medium was washed with water (5×10 ml) and then a 1 g sample (moist weight as filtered) was digested for 30 mins at 90° C. in 2 ml of 50% (v/v) acetic acid. The ligand content of the solid medium was estimated from the optical density (at 520 nm) of the acetic acid digest.

EXAMPLE 45

The process of Example 44 was repeated except that potassium chloride replaced sodium chloride as the alkali metal salt.

EXAMPLE 46

The process of Example 44 was repeated except that sodium sulphate replaced sodium chloride as the alkali metal salt.

EXAMPLE 47

The process of Example 44 was repeated except that disodium hydrogen phosphate replaced sodium chloride as the alkali metal salt and the pH of the ligand/matrix/salt mixture was brought to between 10.5 and 11 by the addition of 5M NaOH.

EXAMPLE 48

The process of Example 44 was repeated except that sodium nitrate replaced sodium chloride as the alkali metal salt.

EXAMPLE 49

The process of Example 43 was repeated except that potassium hydroxide replaced sodium hydroxide as the alkali metal hydroxide.

EXAMPLE 50

The process of Example 44 was repeated except that potassium hydroxide replaced sodium hydroxide as the alkali metal hydroxide.

EXAMPLE 51

The process of Example 50 was repeated except that potassium chloride replaced sodium chloride as the alkali metal salt.

EXAMPLE 52

The process of Example 50 was repeated except that sodium sulphate replaced sodium chloride as the alkali metal salt.

The results of Examples 43 to 52 are summarised in Table 9.

TABLE 9

Binding Procion Blue MXR ligand to Sepharose 4B matrix

| Example | Hydroxide | Salt | mg Ligand bound to gm Matrix |
|---|---|---|---|
| 43 | NaOH (0.01 M) | — | 0.8 |
| 44 | NaOH (0.01 M) | NaCl (0.5 M) | 4.1 |
| 45 | NaOH (0.01 M) | KCl (0.5 M) | 2.4 |
| 46 | NaOH (0.01 M) | $Na_2SO_4$ (0.5 M) | 3.3 |
| 47 | NaOH (0.01 M) | $Na_2HPO_4$ (0.5 M) | 2.2 |
| 48 | NaOH (0.01 M) | $NaNO_3$ (0.5 M) | 1.3 |
| 49 | KOH (0.01 M) | — | 0.9 |
| 50 | KOH (0.01 M) | NaCl (0.5 M) | 2.8 |
| 51 | KOH (0.01 M) | KCl (0.5 M) | 2.2 |
| 52 | KOH (0.01 M) | $Na_2SO_4$ (0.5 M) | 2.4 |

PROTEIN PURIFICATION USING SOLID MEDIA

Media used in the following examples were prepared according to the following general scheme:

800 g of uncross-linked agarose gel (Sepharose 4B) was washed with demineralised water and suspended in 2.8 liters of demin water. To this was added a solution of 16 to 20 g of ligand in 800 ml of demin water. The mixture was stirred for 5 mins and 200 ml of a 200 g/l sodium chloride solution were added. After a further 30 mins stirring, 10N sodium hydroxide was added, 40 ml for a monochloro-triazine ligand or 5 ml for a dichloro-ligand, followed by gentle stirring, in the monochloro case, at room temperature for 48 hours (alternatively 16 hours at 60° C. could have been used for a heat stable, eg cross-linked, matrix) or in the dichloro case, 4 hours (2 hours at 30° C.). The mixture was then filtered and the solid washed successively with water, 1M sodium chloride in aqueous 20% ethanol, 1M aqueous sodium chloride and water. In the case of dichloro-triazinyl ligands, the media was then stirred with 0.1M NaOH/1M ammonium chloride, pH 8.6 to convert the remaining chloride groups to amino groups.

EXAMPLES 53 TO 56

Media comprising ligand E attached to Sepharose 4B at concentrations of 0.81, 0.52 and 0.23 mg/g by processes in accordance with the invention and also at 0.09 mg/g by the process described by Baird at et al, (Febs Letters as cited previously) were used to purify glycerokinase.

Partially purified glycerokinase, derived, from *Bacillus stearothermophilus* and having an activity of 25 Units per mg protein (U/mg) was dissolved at a concentration of 5 to 15 mg/ml in 10mM potassium phosphate (KP) buffer at pH 7.5 and run onto a column of the solid medium. The column was then washed with buffer and the bound enzyme eluted with a solution of 5mM $MgCl_2$ and 5mM ATP in the same buffer. The amounts of enzyme bound by the various media and recovered are shown in Table 10. The product from Example 53 had a specific activity of 120 U/mg and showed a single band on SDS polyacrylamide gel electrophoresis (PAGE) at 58,000 daltons.

EXAMPLES 57 TO 62

Example 53 was repeated using media comprising various concentrations of ligand E on Sepharose 4B and eluting with 1M $KCl/2mM$ $MgCl_2/2mM$ ATP in the same buffer. Results are shown in Table 10.

EXAMPLE 63

Example 57 was repeated using a medium comprising 5.6 mg ligand E per grm of Sepharose 4B with cyanogen bromide activation. Results are shown in Table 10.

TABLE 10

| EXAMPLE | LIGAND CONTENT (mg ligand/gm matrix) | ENZYME Units/ml Bound | ENZYME Units/ml Eluted | % Eluted |
|---|---|---|---|---|
| 53 | 0.81 | 300 | 270 | 90 |
| 54 | 0.52 | 190 | — | — |
| 55 | 0.23 | 100 | 18 | 18 |
| 56 | 0.09 ($Na_2CO_3$ bound) | 40 | — | — |
| 57 | 0.4 | 95 | 90 | 95 |
| 58 | 0.9 | 230 | 205 | 89 |
| 59 | 1.4 | 320 | 265 | 83 |
| 60 | 2.0 | 320 | 260 | 81 |
| 61 | 3.2 | 285 | 205 | 88 |
| 62 | 4.1 | 220 | 105 | 48 |
| 63 | 5.6 (CNBr activated) | 170 | 70 | 41 |

EXAMPLES 64 AND 65

The partially purified enzyme as used in Examples 53 to 56 was dissolved in 10mM KP pH 5.5 and run onto columns comprising ligand F on Sepharose 4B at 0.2 mg/g and 0.7 mg/g respectively. The amounts bound were 100 and 200 units (not saturated). When washed with 50mM KP at pH7.5 virtually all the bound enzyme was eluted from the 0.2 mg/g column but none from the 0.7 mg/g column. All the enzyme could have been eluted from either column with 1M potassium chloride.

EXAMPLE 66

A partially purified cell extract from Pseudomonas bacteria containing 24 units/mg protein of carboxy-peptidase G was dissolved at about 10 mg/ml in 25mM tris-acetate buffer pH7.0 and run onto a column comprising ligand G of Sepharose 4B at 0.39 mg/g. The column was washed with the same buffer and the enzyme eluted with 2mM paraaminobenzoyl glutamate (PARA-G). The product had a specific activity of 150 Units/mg. The elution could also be performed with 1M KCl.

EXAMPLES 67 AND 68

Example 66 was repeated using columns comprising ligand B on Sepharose 4B at 0.1 mg/g and 0.65 mg/g respectively. The enzyme could not be eluted from the 0.65 mg/g column with 2mM PABA-G, but could be eluted from either column with 2M KCl.

EXAMPLE 69

A crude cell extract from 1 Kg of cells of Rhodopseudomonas spheroides containing about 0.1 U/mg protein of β-hydroxy-butyrate dehydrogenase was suspended at 30–40 mg protein/ml in 10mM KP buffer pH 7.5. This was run onto a 2 liter column comprising ligand A on Sepharose 4B at 0.44 mg/g. The column was washed with the buffer and eluted with 1MKCl in 10mM KP pH 7.5. Recovery was greater than 95% with a specific activity of 3–4 U/mg.

The product was dialysed against 10mM KP buffer pH7.5 and then run onto a 900 ml column of ligand F on Sepharose 4B at 0.57 mg/g. The column was washed with buffer and then with 10mM KP/1M KCl buffer pH7.5 and eluted with 10mMKP/1MKCl/5mMNADH pH 7.5 to yield a product having a specific activity of 20–25 U/mg, showing a single band on SDS PAGE at a sub-unit molecular weight of 23,000. Overall recovery was greater than 80%.

EXAMPLES 70 TO 73

The process of Example 66 was repeated using the media produced in Examples 39–42 respectively. The amounts of enzyme bound are shown in Table 11. Recoveries on elution with 1MKCl were 85–90% in all cases.

TABLE 11

| EXAMPLE | LIGAND | MATRIX | mg LIGAND/ gm MATRIX | ENZYME BOUND U/ml packed column |
|---|---|---|---|---|
| 70 | B | Uncross-linked agarose | 0.65 | 320 |
| 71 | B | Cross-linked dextran | 0.63 | 310 |
| 72 | B | Dextran/acrylamide Copolymer | 0.29 | 65 |
| 73 | B | Cross-linked agarose | 0.32 | 110 |

EXAMPLE 74

Centrifuged equine serum was partially purified by absorption on DEAE cellulose to yield a protein preparation containing 0.08U cholinesterase/mg protein. This was freeze-dried and then dissolved at 20 mg protein/ml in 10mM KP buffer at pH6.8 and run onto a column comprising ligand C on Sepharose 4B at 0.58 mg/g. 14 U/ml of packed column were bound. The column was washed with buffer and eluted with the same buffer containing 1MKCl to give 80% yield of a protein preparation having a specific cholinesterase activity of 4 U/mg protein.

EXAMPLE 75

Crude human urine was concentrated about 20 to 40 times by ultrafiltration using a hollow fibre unit (Trade Mark "Amicon" type HIDP10). The concentrate (containing 2.5 mg protein/ml) was run onto a column comprising ligand F on Sepharose 4B, at 0.6 mg/g, pre-equilibrated with 10mM KP buffer pH7.5. The column was washed with buffer and eluted with 1M KCl pH7.5 to yield a urokinase preparation having a specific activity 200–300 times that of the concentrate.

EXAMPLES 76 AND 77

Example 75 was repeated using ligands B and E respectively. Satisfactory separations were obtained in both cases.

We claim:

1. A process for producing a protein-binding solid medium comprising reacting a protein-binding ligand material of structure

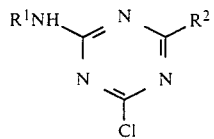

wherein $R^1$ is a sulphonated derivative of anthraquinone, a substituted anthraquinone, an aromatic azo group, or a phthalocyanine group, and $R^2$ is either an organic group or a chloro substituent, with an affinity chromatographic matrix containing hydroxy or amino groups which is a polymer or copolymer of agarose, dextrose, dextran or acrylamide at a pH of at least 8, in an aqueous solution of an alkali metal hydroxide and sodium chloride wherein the sodium chloride enhances the binding of the ligand material to the matrix by a common ion effect.

2. A process according to claim 1 wherein the alkali metal hydroxide is sodium hydroxide.

3. A process according to claim 1 wherein the sodium chloride concentration is between 0.25 and 0.5 Molar.

4. A process according to claim 1 wherein $R^1$ has the structure

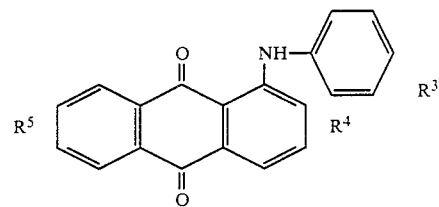

and wherein $R^3$, $R^4$ and $R^5$ each represents a sulphonyl group or a hydrogen atom or an alkyl or amino substituted derivative of such structure.

5. A process according to claim 1 wherein $R^1$ has the structure

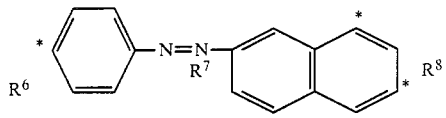

wherein $R^6$, $R^7$ and $R^8$ each represents a sulphonyl group or hydrogen atom and the point of attachment to the triazinyl ring may be any of the points marked *, or substituted derivatives of such a structure.

6. A process according to claim 1 wherein $R^2$ is an organic group.

7. A process according to claim 6 wherein $R^2$ is a sulphonated phenyl group.

8. A process according to claim 1 wherein the ligand material contains a monochloro-triazinyl group and the reaction between the ligand material and the matrix is conducted at a pH of at least 9.5.

9. A process according to claim 8 wherein the reaction between the ligand material and the matrix is conducted at ambient temperature for 40 to 60 hours.

10. A process according to claim 8 wherein the reaction between the ligand material and the matrix is conducted at a temperature of 40° to 60° C.

11. A process according to claim 1 wherein the ligand material contains a dichloro-triazinyl group and the reaction between the ligand material and the matrix is conducted at a pH between 8 and 12.5.

12. A process according to claim 1 wherein the matrix is an agarose homopolymer.

* * * * *